United States Patent [19]

Dellas

[11] Patent Number: 4,485,809
[45] Date of Patent: Dec. 4, 1984

[54] FILM WINDOW DRESSING

[75] Inventor: James P. Dellas, East Brunswick, N.J.

[73] Assignee: Johnson & Johnson Products, Inc., New Brunswick, N.J.

[21] Appl. No.: 329,969

[22] Filed: Dec. 11, 1981

[51] Int. Cl.³ .............................................. A61L 15/00
[52] U.S. Cl. .................................... 128/156; 604/307; 428/343
[58] Field of Search ................................ 128/155-156; 604/304, 307, 308, 344, 389-390; 428/343

[56] References Cited

U.S. PATENT DOCUMENTS

| | | | |
|---|---|---|---|
| 2,629,378 | 2/1953 | Barton | 128/155 |
| 3,143,208 | 8/1964 | Sizemore, Jr. | 128/155 |
| 3,550,589 | 12/1970 | Wallerstein | 128/156 |
| 4,281,650 | 8/1981 | Spiegelberg | 128/156 |
| 4,302,500 | 11/1981 | Flora | 128/156 |
| 4,341,208 | 7/1982 | Gordon | 128/156 |

Primary Examiner—C. Fred Rosenbaum
Attorney, Agent, or Firm—Michael Q. Tatlow

[57] ABSTRACT

A film dressing with a high moisture vapor transmission rate is disclosed. The film dressing has a release sheet attached to the dressing. There is a central region of the film, defined by perforation lines, which is applied to the patient. There are cut lines in the release sheet which are parallel to but spaced outside the perforations in the dressing to allow the release sheet to be removed, the adhesive portion of the film to be applied to the patient and the exterior portion of both the release sheet and the film to be removed.

5 Claims, 5 Drawing Figures

FILM WINDOW DRESSING

FIELD OF THE INVENTION

The present invention relates to surgical dressings made from films which are oxygen permeable, have high moisture vapor permeability but which are impermeable to liquid water and bacteria.

PRIOR ART

Surgical dressings made with composite layers of film and adhesive which have high moisture vapor transmission rates have been disclosed in U.S. Pat. Nos. 3,483,018 and 3,645,835. These dressings are made from films which may be transparent and which have moisture vapor transmission rates of greater than 15 grams per 100 square inches per 24 hours. These dressings are used in many applications and have an advantage in that they are impervious to bacteria and liquid water but yet allow oxygen to penetrate the dressing from the ambient atmosphere and allow moisture from the skin of the patient to escape from beneath the dressing.

The operative body contact area of these dressings is made of continuous film, that is, film which is not perforated or is not microporous. The adhesive coating which is applied to these dressings also must have a moisture vapor transmission rate which is sufficient to allow the complete dressing to have a moisture vapor transmission rate of at least 15 grams per 100 square inches per 24 hours.

In order to obtain the desired moisture vapor transmission rate, the dressings are made from extremely thin films of polyurethane or of other polymeric materials which have the desired moisture vapor transmission properties. These films are extremely thin, less than 10 mils, and are very flexible, limp and flimsy because of their thinness. These characteristics allow the dressing to be applied to the varying contours of the human body but also create some problems in the application of the dressing to a patient. The dressings are manufactured with a release sheet covering the adhesive surface of the dressing. The release sheet is removed from the dressing when the dressing is applied to the patient. The thinness of the film and its flexibility allows the film to turn over onto itself during attempts to apply the film dressing to a patient. The film is similar in this property to polyvinylidene chloride film household wrap. When a portion of the adhesive surface of the film touches another portions of the adhesive surface, the film dressing sticks to itself and makes it extremely difficult to apply to the patient.

In order to overcome this problem, film dressings of this type are made with adhesive-free tabs at opposite ends of the film. In some products there is a reinforcing member at the tab ends to provide a grasping or holding surface to be used to apply the dressings to a patient. After the dressing is applied, the adhesive-free tab end is cut off of the adhesive portion of the dressing with scissors or by tearing the film. The use of scissors or tearing tends to leave a ragged or uneven edge on the film dressing. This uneven edge tends to roll off the skin of the patient and, eventually, the entire dressing may be inadvertently removed from the patient.

SUMMARY OF THE INVENTION

The present invention is directed to a film dressing which eliminates the problems in applying the dressing to a patient which are mentioned above. The present dressing provides a window frame of release paper which can be used to hold the dressing as it is being applied to the patient. After the dressing is properly applied to the patient, the window frame can be removed leaving the dressing in place.

DETAILED DESCRIPTION OF THE INVENTION

The invention will be better understood with reference to the drawings in which.

Figure 1:
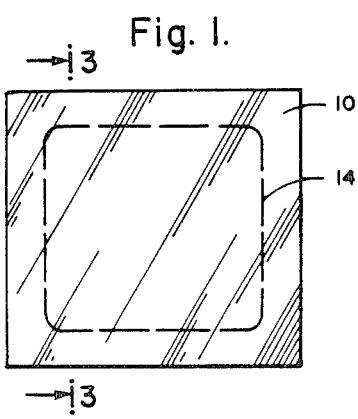
FIG. 1 is a top plan view of the dressing of the present invention showing the film side of the dressing.

The moisture vapor permeable film used in the present dressing is made from synthetic polymers which are capable of being formed into continuous films by casting, extrusion or other known film-making processes. The film thickness is from 0.5 to 10 mils, and preferably from 1 to 3 mils. The film is continuous in that it has no perforations or pores in the body-contacting portion of the film which extend through the depth of the film. Films of this type are known and generally are hydrophilic, polymeric materials through which water vapor is capable of diffusing. The films that may be used in the present invention are the polyurethane films which are described in U.S. Pat. No. 2,871,218 and the acrylate copolymers which are described in U.S. Pat. Nos. 2,949,443 and 3,645,835. Generally, these films will have moisture vapor transmission rates between 15 and 80 grams per 100 square inches per 24 hours, as determined by ASTM Test E96 at 100° F. and 90% Relative Humidity.

The moisture vapor permeable film is shown in the drawing as 10. On one surface of the film is a skin adhesive 11. The particular adhesive that is employed may be selected from one of the well-known skin contact adhesives such as those disclosed in U.S. Pat. Nos. 3,189,581; 3,218,357; 3,325,459 and 4,112,213. These adhesives are generally copolymers of 2-ethylhexyl acrylate and vinyl acetate in ratios of approximately 60 to 70 parts of the acrylate and 30 to 40 parts of the vinyl acetate. The polymers may also contain small amounts of N-tertiary butylacrylamide as a third monomer and a cross-linking agent. The preferred adhesive is a copolymer of approximately 70% 2-ethylhexyl acrylate and 30% vinyl acetate and containing from 0.01 to 1% of a silane cross-linking agent as disclosed in U.S. Pat. No. 4,112,213. Water-based adhesives and hot-melt adhesives may also be employed.

The adhesive is deposited on the film by solvent spreading, coating, extrusion or other known methods. The level of the adhesive on the film should not be so great that the moisture vapor transmission characteristics of the film are impeded. Generally, a coating level of from 0.5 to 3 ounces per square yard is sufficient to obtain adequate skin adhesion but not so great as to interfere with the moisture vapor transmission characteristics desired in the finished dressing. The adhesive mass may be applied directly to the film or may be applied to a silicone-coated carrier sheet and the film then brought into contact with the adhesive on the carrier sheet. The film may be removed from the carrier sheet for subsequent processing, or the carrier sheet may remain with the film and become the release sheet 12 in the finished dressing.

As shown in FIG. 1, the dressing has a top surface which is the polymer film previously described. There is a perforation line 14 spaced inwardly from the edges of the dressing and through the film. The perforations are made on substantially straight lines with a radius of curvature at each corner. The ratio of the cut areas of the perforation line to the uncut areas of the perforation line can range from about 20 to 1 to about 0.5 to 1. The preferred ratio is about 10 to 1. The perforations should be such that the film can be torn away at the perforation line without tearing the film itself. The perforation line in the film is spaced from about ½ inch from the edge of the dressing to allow sufficient space to hold the dressing by the window frame without touching that portion of the film that will be applied to the patient.

Figure 2:
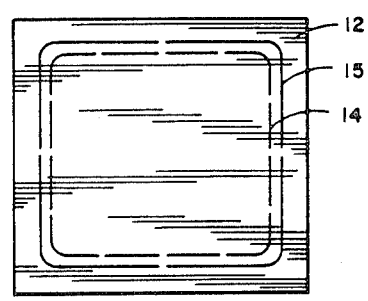
FIG. 2 is a bottom plan view of the dressing of the present invention showing one embodiment of the release paper side of the dressing.
Figure 3:
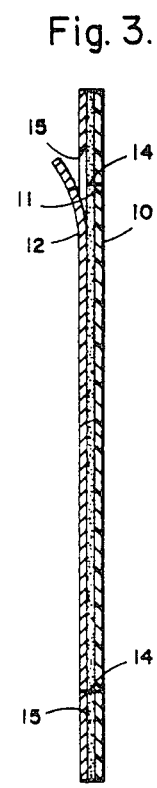
FIG. 3 is a cross-sectional view of the dressing taken along lines 3—3 of FIG. 1.

As best shown in FIG. 2, the paper release sheet also has a cut line 15, which may be a series of interrupted cuts, or a continuous kiss cut through the paper. The cut line in the release sheet is parallel to but spaced outside the perforation line 14 in the film. The cut line in the release paper should have a larger cut portion than the perforation line in the film to enable the release paper to be readily removed without breaking the perforation line of the film. At each of the corners of the cut line in the release paper, the cut is totally through the paper, and there are no uncut portions. This allows the release paper to be slightly bent to expose a free end of the paper to enable the paper release sheet to be readily removed from the film. The cut line in the release paper is spaced outside of the perforation line, that is, between the perforation line in the film and the outside edges of the dressing. The space between the perforation line and the cut line is from about 1/16 inch to about ¼ inch, ⅛ inch being preferred. As a matter of convenience, the perforation line 14 and the cut line can be made from the release paper side of the dressing. The perforation line in the film can be made from the film side of the dressing. As shown in FIG. 3, the cut line 15 does not penetrate the film portion of the dressing. The perforation line in the film will penetrate the release paper if it is made from the release paper side of the dressing.

Figure 4:
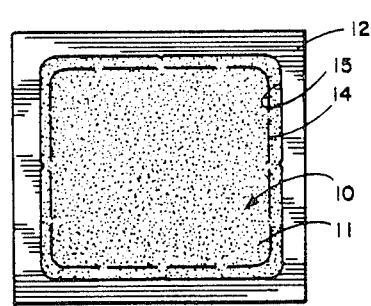
FIG. 4 is a bottom plan view of the window-frame portion of the dressing.

FIG. 4 shows the "window frame" after the central portion of the release sheet has been removed and the central portion of the film has been applied to the patient. The portion of the film 10 between the perforation line 14 and the cut line 15 remains with the release sheet 12, as the film is not cut along the cut line 15.

Figure 5:
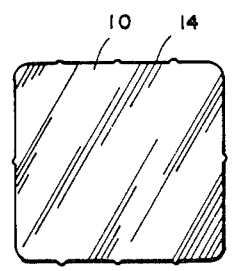
FIG. 5 shows the film portion of the dressing which is applied to the patient.

FIG. 5 shows the portion of the film that is actually applied to the patient.

A significant advantage in the present dressing is that the person applying the dressing to the patient need not contact the portion of the film that will be applied to the patient, thereby eliminating a potential source of wound contamination. After the central portion of the release sheet is removed from the dressing, the dressing can be manipulated into the proper position on the patient by holding the window-frame portion of the dressing. When the central film portion of the dressing is in place on the skin of the patient, the window frame is removed and discarded. In applying the dressing to the patient, the dressing is bent on a corner which will release the corner so that it may be easily grasped. The release paper, that is the central portion of the release paper, is then removed from the film along the cut line. The film dressing is then applied over the wound and secured in position by the adhesive, which is now fully exposed within the window of the dressing. After the dressing is firmly in place, the paper perimeter, which still remains on the dressing, is firmly grasped, and the paper and exterior margin of the film are removed from the patient effectively leaving only the film window in place over the wound. Although the dressing shown in the drawings is square, it should be understood that the dressing may be manufactured in other configurations such as rectangular, circular, oval or any other suitable shape. Dressings of this type are distributed as sterile dressings.

A typical dressing of the present invention is made as follows:

A 2.5 mil thick polyurethane film is coated with an adhesive which is a copolymer of 70% of 2-ethylhexyl acrylate and 30% vinyl acetate and containing a small amount, 0.1% to 1%, of a silane, a crosslinking monomer. The dressing has an overall dimension of approximately 4 by 4 inches. The perforation line through the film in the dressing is spaced approximately ¾" from the outside edge of the dressing. The perforation lines in the film are made of alternating 0.15" cut portions and 0.033" uncut portions. The cut line in the release paper is continuous except for a ¼" attachment on each side of the dressing.

The cut line through the release paper is spaced ⅛" outside the perforation line. The dressing constructed in this manner is readily applied to a patient without contamination of the adhesive.

I claim:

1. An adhesive dressing comprising a transparent polymeric film from 0.6 to 10 mils in thickness and having a moisture vapor transmission rate of at least 15 grams per 100 square inches per 24 hours and being impervious to liquid water, a skin adherent adhesive coating on one surface of said film, a release sheet covering said adhesive coating, a perforation line in said film spaced inwardly from the periphery of the film, a cut line in said release sheet in alignment with the perforations in said film to enable the central portion of the release sheet to be removed from the film and the remainder of the dressing without breaking the perforations in said film.

2. The adhesive dressing of claim 1 in which the film is from 1 to 3 mils in thickness.

3. The adhesive dressing of claim 1 in which the perforation line in the film is spaced between ½ inch and one inch from the edges of the dressing, and the cut line is spaced 1/16 to ¼ inch outside the perforation line.

4. The adhesive dressing of claim 3 in which the cut line is spaced ⅛ inch outside the perforation line.

5. The adhesive dressing of claim 1 in which the perforation line also extends through the release sheet.

* * * * *